(12) United States Patent
Divakaran et al.

(10) Patent No.: US 10,492,747 B2
(45) Date of Patent: Dec. 3, 2019

(54) SYSTEM AND METHOD FOR EXTENDING AND RETRACTING A MOVEABLE ARM

(71) Applicant: KUB Technologies, Inc., Stratford, CT (US)

(72) Inventors: Edwin Divakaran, Stratford, CT (US); Timothy Ely, Stratford, CT (US); Vikram Butani, Stratford, CT (US); Chester Lowe, Stratford, CT (US); Yan Chen, Stratford, CT (US)

(73) Assignee: KUB Technologies, Inc., Stratford, CT (US)

( * ) Notice: Subject to any disclaimer, the term of this patent is extended or adjusted under 35 U.S.C. 154(b) by 206 days.

(21) Appl. No.: 15/651,608

(22) Filed: Jul. 17, 2017

(65) Prior Publication Data

US 2018/0014801 A1    Jan. 18, 2018

Related U.S. Application Data (60) Provisional application No. 62/363,376, filed on Jul. 18, 2016.

(51) Int. Cl.
*A61B 6/00* (2006.01)

(52) U.S. Cl.
CPC .......... *A61B 6/4405* (2013.01); *A61B 6/4429* (2013.01)

(58) Field of Classification Search
CPC ......... A61B 6/4405; A61B 5/70; A61B 6/027; A61B 6/40; A61B 6/4275; A61B 6/44; A61B 6/4429
See application file for complete search history.

(56) References Cited

U.S. PATENT DOCUMENTS

| | | | |
|---|---|---|---|
| 2,859,629 A | 11/1958 | Parker et al. | |
| 3,010,328 A | 11/1961 | Forey | |
| 4,161,004 A | 7/1979 | Dalziel | |
| 4,388,003 A | 6/1983 | Feller | |
| 4,988,262 A | 1/1991 | Gines | |
| 5,015,140 A | 5/1991 | Kling | |
| 5,080,498 A | 1/1992 | Tsukada | |
| 5,207,555 A | 5/1993 | Shirai | |
| 5,839,873 A | 11/1998 | Lloyd et al. | |
| 6,203,199 B1 | 3/2001 | Pfeuffer | |
| 7,479,885 B2 | 1/2009 | Greubel | |
| 7,604,408 B2 | 10/2009 | Dorn et al. | |
| 9,010,205 B2 | 4/2015 | Schroeder et al. | |
| 9,150,355 B2 | 10/2015 | Hortig et al. | |
| 9,169,868 B2 | 10/2015 | Hsu | |
| 2006/0023978 A1 | 2/2006 | Haub | |
| 2007/0140602 A1 | 6/2007 | Hsu et al. | |
| 2009/0196539 A1 | 8/2009 | Pfeuffer et al. | |
| 2015/0196262 A1* | 7/2015 | Grady | A61B 6/4441 378/42 |
| 2018/0000434 A1* | 1/2018 | Ninomiya | A61B 6/4405 |
| 2018/0108447 A1* | 4/2018 | Turner | A61B 6/4405 |

* cited by examiner

*Primary Examiner* — David P Porta
*Assistant Examiner* — Fani Boosalis
(74) *Attorney, Agent, or Firm* — Ziegler IP Law Group, LLC (57) ABSTRACT

The present disclosure relates to a linear slide assembly to assist in the motion of an arm that moves vertically in an arc with the center of access statically attached to the linear slide assembly which is to be utilized in the field of portable x-ray imaging and more specifically, a system and method for extending and retracting a vertically moveable arm in a limited linear motion.

19 Claims, 6 Drawing Sheets

SYSTEM AND METHOD FOR EXTENDING AND RETRACTING A MOVEABLE ARM

CROSS-REFERENCE TO RELATED APPLICATIONS

This application claims priority to and the benefit of U.S. Provisional Patent Application Ser. No. 62/363,376 filed Jul. 18, 2016, the disclosure of which is incorporated herein by reference in its entirety.

BACKGROUND

Field of the Present Disclosure

The present disclosure relates to a linear slide assembly to assist in the motion of an arm that moves vertically in an arc with the center of axis statically attached to the linear slide assembly which is to be utilized in the field of portable x-ray imaging utilized to image patients and more specifically, a system and method for extending and retracting a vertically moveable arm in a limited linear motion.

Description of the Related Art

The present disclosure is directed to a method of and apparatus for extending and retracting a vertically moveable mechanism/arm in a limited linear distance.

The x-ray is the most valuable imaging modality in the assessment of neonatal/human subjects with respiratory distress as well as orthopedic abnormalities. Portable X-ray units can be very heavy and cumbersome to move, for example, around a crowded neonatal department between incubators and/or beds. This disclosure includes an apparatus that allows a technician to move the arm to which an x-ray source is attached laterally in a limited increment along the same axis of the arm to facilitate the accurate focusing of the x-ray tube on the patient without having to move the complete portable x-ray unit.

In typical x-ray imaging the subject/patient is immobilized. The subject/patient or a part or portion thereof is placed between an x-ray source and a digital imaging device (detector) to create a two-dimensional radiographic image of the subject/patient. Neonatal unit patients are small but this doesn't make the job is easier . . . in many respects it makes the job harder. The multitude of attachments (e.g., ekg, respirator, etc.) to the baby is also a challenge. The attachments seem to dominate the space around the baby and the bed or incubator in which it rests.

The problem that arises with the above scenario is that space between, for example, isolette incubators is minimal with all of the equipment that is needed for the care of the newborns in the incubators. This systems, methods and apparatus of the present disclosure will allow for the imaging of the subject newborn from a greater number of different positions of the x-ray source and x-ray receptor relative to the subject while allowing the main body of the portable x-ray system to remain stationary. To do this, the arm that the x-ray source is attached to is mounted to a linear slide that is mounted on the vertical arm of the mobile unit. This facilitates placement of the main unit close to the isolette and allows the technician to make minute adjustments to the positioning of the x-ray source and its arm without moving the main x-ray unit.

U.S. Pat. No. 9,150,355 B2, entitled "Telescoping Mechanism and Method of Extending and Retracting a Telescoping Mechanism", Hortig et al. refers to a system that extends and retracts a telescoping arm. In the present disclosure, the arm moves linearly horizontally and vertically within an arc.

It would be advantageous to have a compact portable x-ray system with a limited linear motion to enable the operator to not have to move the complete unit to incrementally adjust the x-ray source and be able to target the subject/patient.

SUMMARY OF THE INVENTION

As described herein, the exemplary embodiments overcome one or more of the above or other disadvantages known in the art.

In one embodiment, the aspects of the present disclosure are directed to a method and system for extending and retracting the movable arm on a portable neonatal x-ray unit. In one embodiment, the method and system includes an x-ray source, a flat panel digital x-ray detector, an arm that moves vertically with a point attached to the main portable x-ray unit with the x-ray source attached, and a linear slide attached to both the main portable x-ray unit and the arm (collectively referred to herein as the "unit").

In another embodiment, a linear slide apparatus for an x-ray source is provided where the x-ray source is mounted to a first end of an arm. The linear slide includes a top panel to which a second end of the arm is mounted, two linear rails, two bearing housings each slideably engaged with one of the linear rails to produce a linear movement along the path of the linear rails and the two bearing housings are also connected to the top panel and a linear slide base to which the linear rails are mounted, the linear slide base also attached to a structural base unit via an attachment structure such as a post capable of permitting rotational movement of the linear slide base around the structural base unit.

In another embodiment, a portable x-ray unit is provided. The portable x-ray unit includes an arm, an x-ray source mounted to a first end of an arm, a moveable structural base unit to which the linear slide base is attached via an attachment structure such as a post capable of permitting rotational movement of the linear slide base around the moveable structural base unit and an x-ray detector. The linear slide apparatus includes a top panel to which a second end of the arm is mounted, two linear rails, two bearing housings each slideably engaged with one of the linear rails to produce a linear movement along the path of the linear rails and the two bearing housings are also connected to the top panel and a linear slide base to which the linear rails are mounted.

In another embodiment, a portable x-ray unit is provided. The portable x-ray unit comprises an arm, an x-ray source mounted to a first end of an arm, a linear slide apparatus, a monitor, an x-ray detector and a moveable structural base unit. The linear slide apparatus comprises a top panel to which a second end of the arm is mounted, two linear rails, two bearing housings each slideably engaged with one of the linear rails to produce a linear movement along the path of the linear rails, the two bearing housings connected to the top panel and a linear slide base to which the linear rails are mounted. The moveable structural base unit to which the linear slide base is attached via an attachment structure is capable of permitting rotational movement of the linear slide base around the moveable structural base unit, the moveable structural base unit including an x-ray operation and control system used to control the x-ray source unit and the x-ray detector, where the x-ray detector is hard wired or wirelessly in communication with the x-ray operation and control system.

The above aspects of the disclosed embodiments overcome the deficiencies of the prior art by advantageously allowing the operator to be able to adjust and/or move the arm of the portable x-ray unit to better align the x-ray beam on the subject and to ensure that the physician/technician (the operator of x-ray unit) has attained the intended procedure/image in an expedient manner without having to manipulate the patient.

These and other aspects and advantages of the exemplary embodiments will become apparent from the following detailed description considered in conjunction with the accompanying drawings. It is to be understood, however, that the drawings are designed solely for purposes of illustration and not as a definition of the limits of the invention, for which reference should be made to the appended claims. Moreover, the drawings are not necessarily drawn to scale and that, unless otherwise indicated, they are merely intended to conceptually illustrate the structures and procedures described herein. In addition, any suitable size, shape or type of elements or materials could be used.

DETAILED DESCRIPTION

The systems, apparatus and methods of the present disclosure address the needs of the art by providing the operator (e.g., physician, technician, etc.) an apparatus and technique for imaging subjects/patients that overcome the shortfalls of portable x-ray units by allowing the fine tuning of the x-ray source and x-ray receptor (i.e., the detector) relative to the subject/patient or a part or portion thereof such that the subject/patient or part or portion thereof is positioned between the x-ray source and x-ray receptor (i.e., the detector) for the preparation of imaging and performing the x-ray imaging process to obtain an x-ray image of the subject/patient or part or portion thereof without having to move the entire x-ray unit. The systems, apparatus and methods of the present disclosure enable the use of a linear slide mounted to a structure on the cart to efficiently provide accurate imaging of a subject/patient by allowing the technician to move the arm incrementally in a limited linear motion thereby ensuring that the region of interest is imaged properly.

Figure 1:
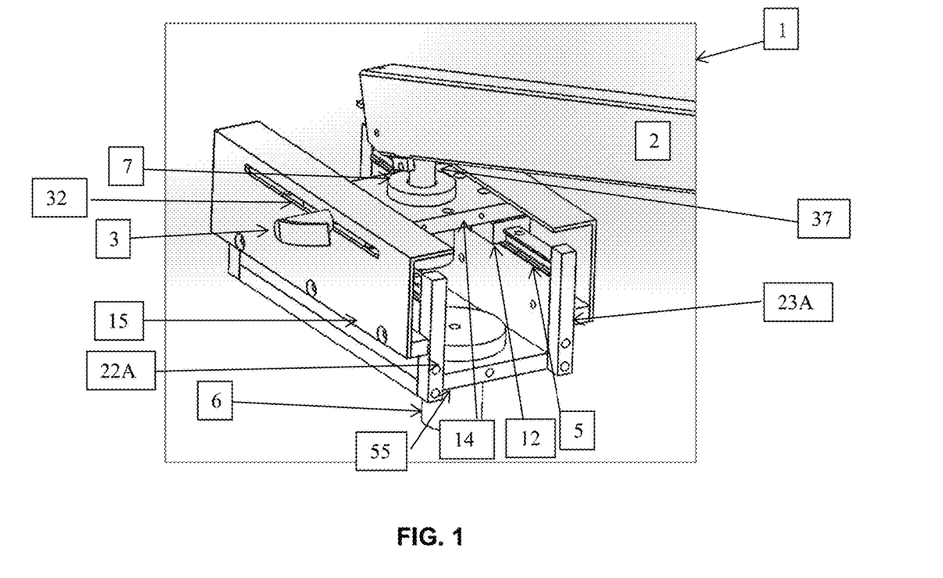
FIG. 1 shows an isometric view of a linear slide apparatus.
Figure 2:
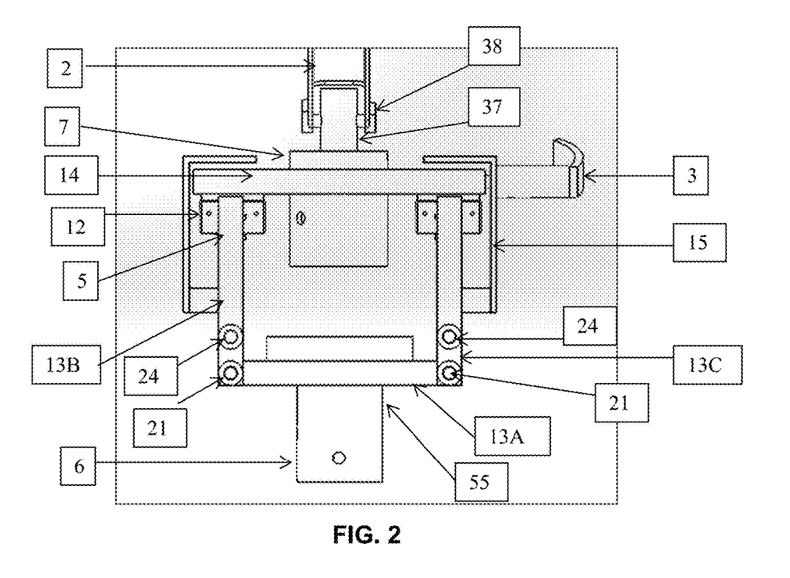
FIG. 2 displays a front view of the linear slide apparatus of FIG. 1.
Figure 3:
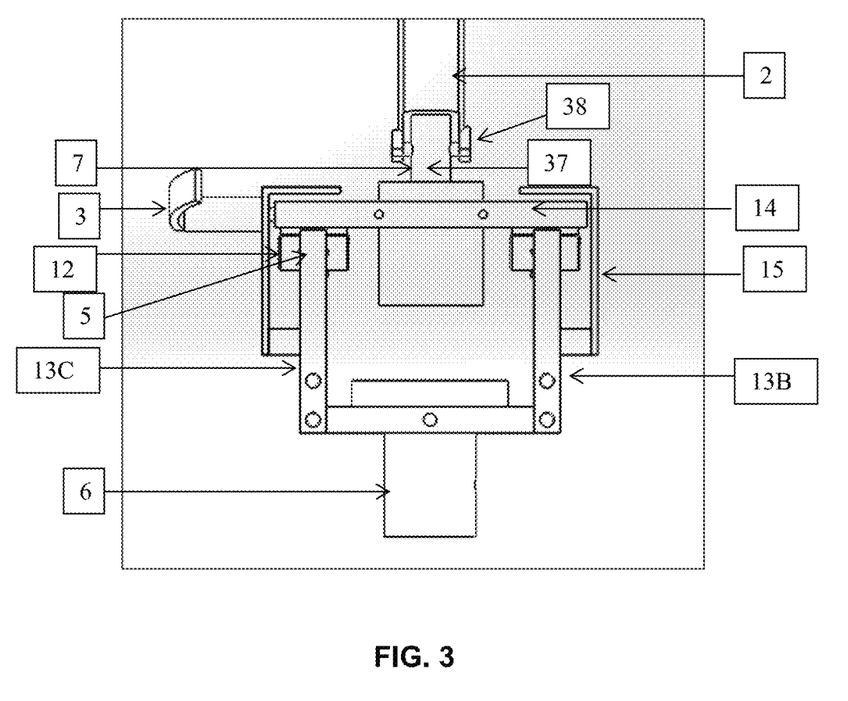
FIG. 3 displays a back view of the linear slide apparatus of FIG. 1.
Figure 4:
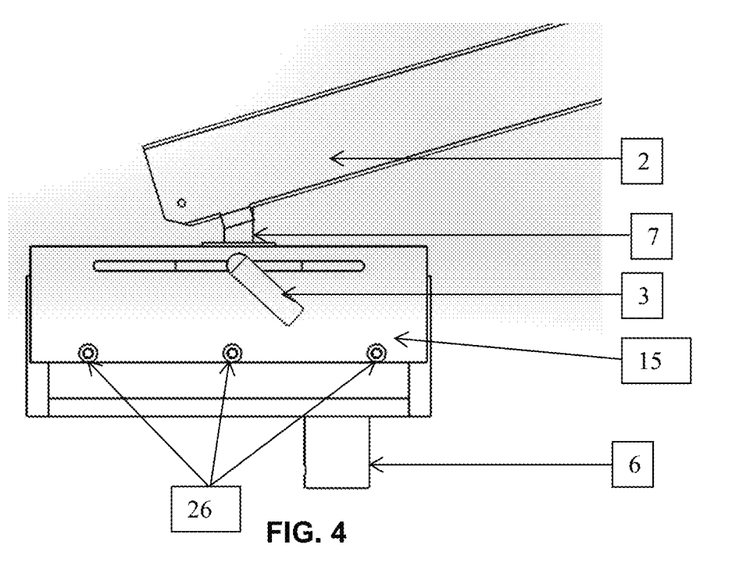
FIG. 4 displays a side view of the linear slide apparatus of FIG. 1.
Figure 5:
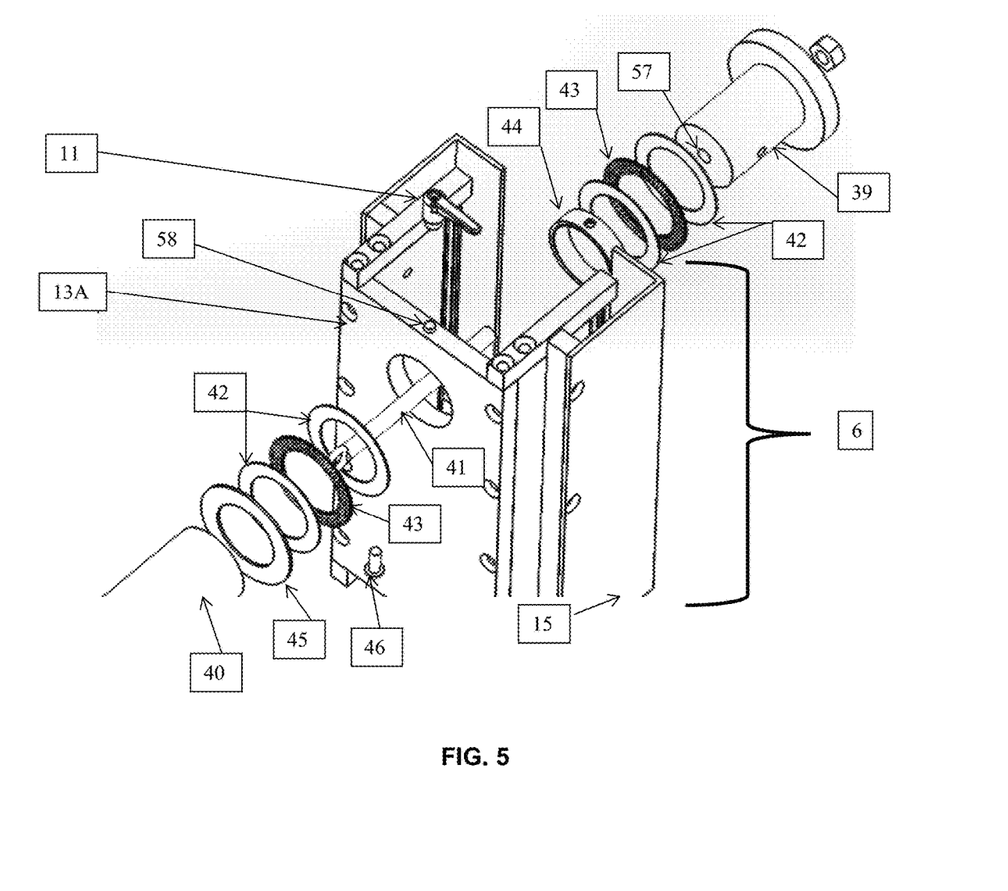
FIG. 5 is an exploded bottom side view of the linear slide apparatus of FIG. 1.
Figure 6:
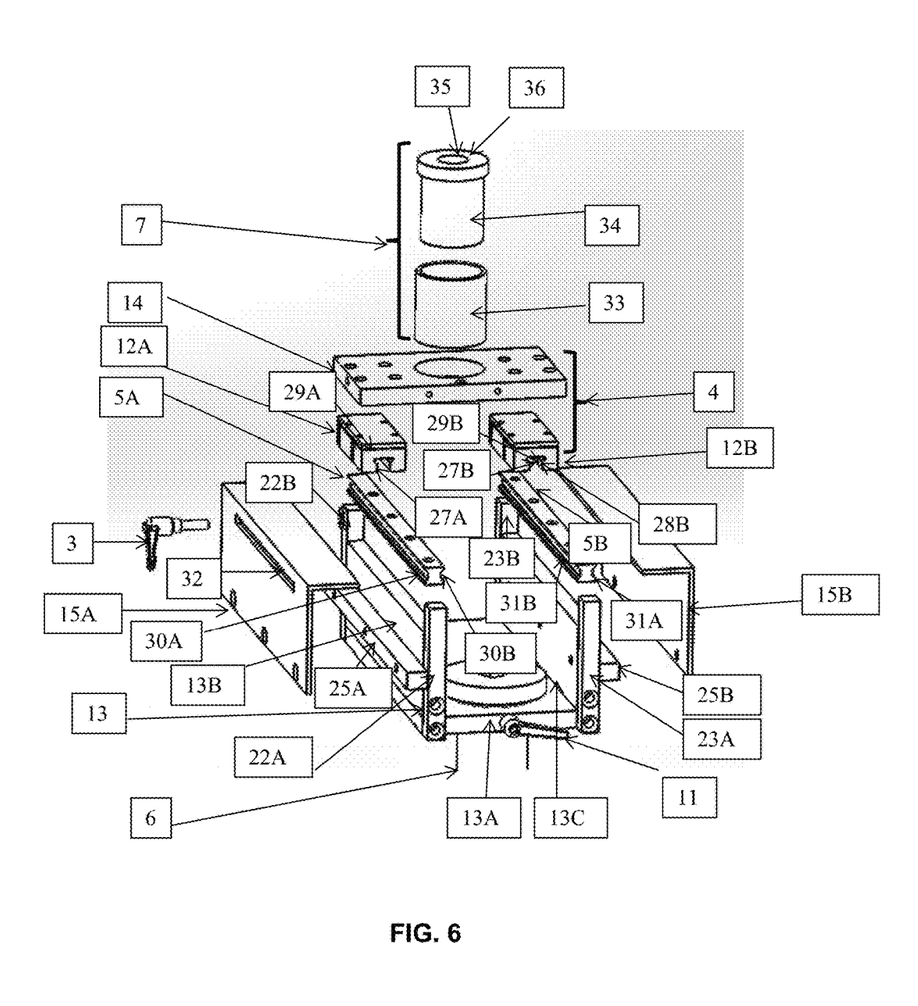
FIG. 6 is an exploded top end view of the linear slide apparatus of FIG. 1.
Figure 7A:
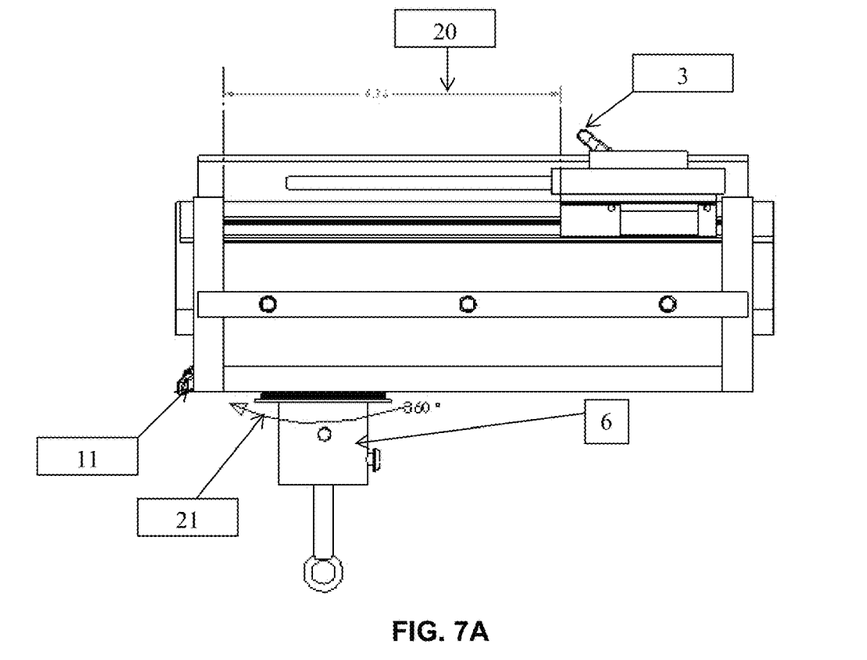
FIGS. 7A and 7B illustrate the movement of the linear slide apparatus of FIG. 1.
Figure 7B:
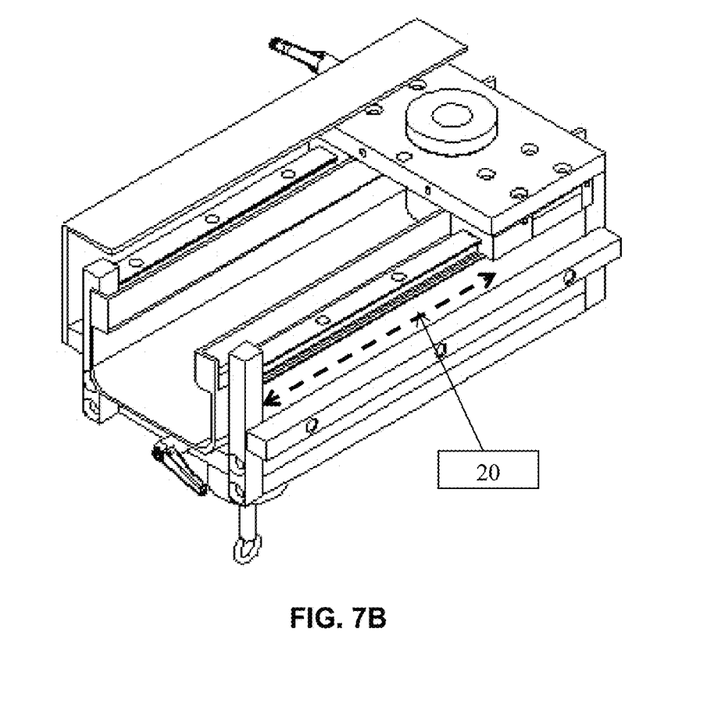
Figure 8:
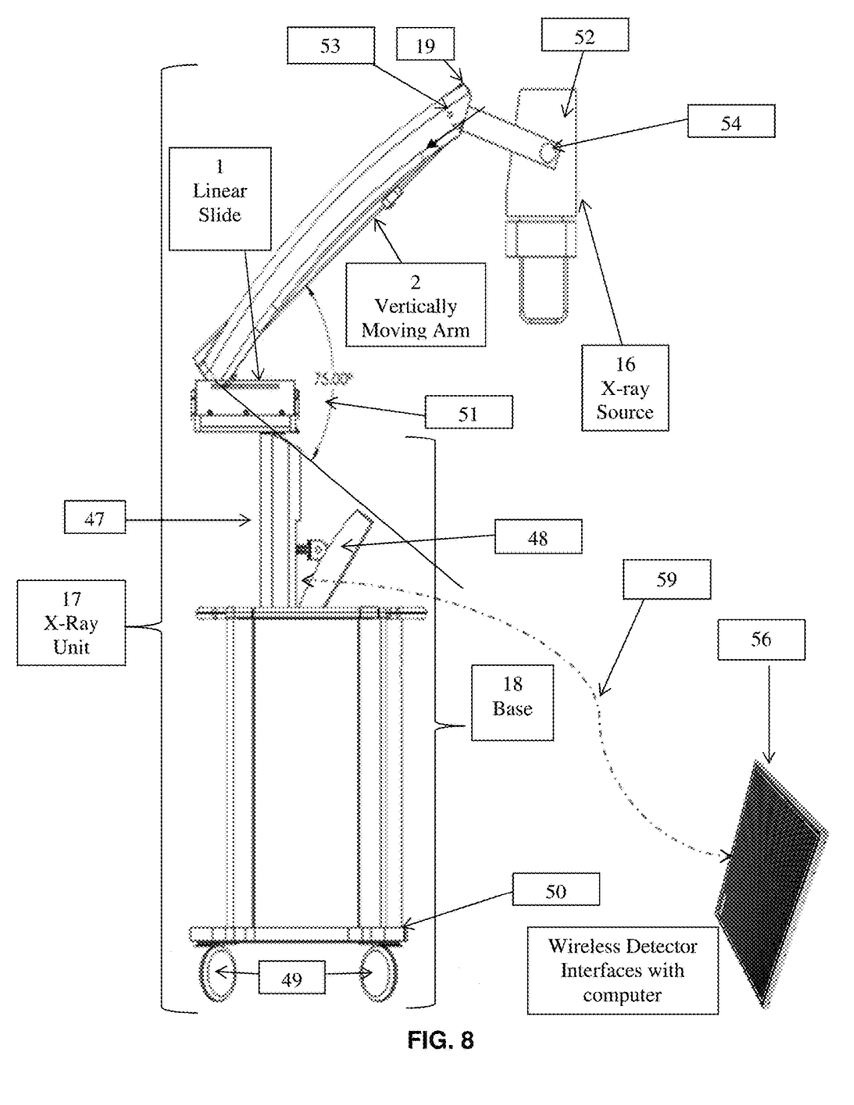
FIG. 8 is the exemplary view of a linear slide apparatus attached to and utilized in an x-ray unit.

One embodiment illustrated in FIGS. 1-8, includes a fixture and/or unit constructed of metal (preferably aluminum and/or steel) herein called a linear slide apparatus 1. Linear slide apparatus 1 is mounted at a secured point to an attachment structure, for example, a post 6, located on a portable x-ray unit 17. The linear slide apparatus 1 is attached at position 7 to an arm 2. The arm 2 can move vertically up and down within an arc with an x-ray source 16 attached to the end of the arm 2 at position 19 opposite to the end of the arm 2 attached to the linear slide apparatus at position 7. The linear slide apparatus 1 allows the arm 2 to move in a limited linear motion 20 as well as a 360 degree circular motion 21 isocentered around its attachment point at post 6 to the main base 18 of the portable x-ray unit 17, as shown in FIGS. 7A, 7B and 8. The movement of the linear slide apparatus can be performed manually by a human operator (e.g., physician/technician)

The assembly of linear slide apparatus 1 includes a linear slide base 55 that includes three steel or aluminium panels including a bottom structure plate 13A and two side structure plates 13B and 13C and a steel or aluminium top panel 14 where the arm 2 is attached at position 7. Side structure plates 13B and 13C are both mounted to bottom structure plate 13A using acceptable fastening devices 21 (for example, screws, rivets or other fastening devices). Side structure plates 13B and 13C are positioned on opposing sides of bottom structure plate 13A, side structure plates 13B and 13C preferably being substantially perpendicular to bottom structure plate 13A and substantially parallel to each other. Side structure plate 13B may also include end pieces 22A and 22B and side structure plate 13C may also include end pieces 23A and 23B. Each pair of end pieces are positioned on opposite sides of the side structure plate to which they are attached using acceptable fastening devices 24 (for example, screws, rivets or other fastening devices). The end pieces may also be attached to bottom structure plate 13A using acceptable fastening devices 21 (for example, screws, rivets or other fastening devices). Side structure plates 13B and 13C may also include side shield panels 15A and 15B respectively. Side shield panels 15A and 15B may be attached to side structure plates 13B and 13C via bar structures 25A and 25B that are themselves attached to side structure plates 13B and 13C using acceptable fastening devices 26 (for example, screws, rivets or other fastening devices).

Steel roller bearings are attached to top panel 14 to provide linear motion relative to linear slide base 55. The steel roller bearings include two bearing housings 12A and 12B and two corresponding linear rails 5A and 5B. Bearing housings 12A and 12B are substantially identical and each includes bearing elements positioned in linear slots 27A and 27B, respectively. The linear slots 27A and 27B may be tapered in cross-section as illustrated in FIG. 6 such that the openings 28A and 28B at the bottom of the respective linear slots are smaller in cross-section than their respective slot bases 29A and 29B. Bearing housings 12A and 12B are attached to top panel 14 and positioned such that linear slots 27A and 27B are substantially parallel to one another.

Side structure plates 13B and 13C include linear rails 5A and 5B respectively connected thereto. Linear rails 5A and 5B are substantially identical and may be positioned between and connected to the respective end pieces should side structure plates 13B and 13C include same. Linear rail 5A includes linear rail slots 30A and 30B on opposing sides of linear rail 5A and linear rail 5B includes linear rail slots 31A and 31B on opposing sides of linear rail 5B. Linear rail slots 30A, 30B, 31A and 31B may be substantially U-shaped or other shape so that these linear rail slots are of a complementary size and shape to engage linear slots 27A and 27B of bearing housings 12A and 12B such that bearing housings 12A and 12B are slideable along linear rails 5A and 5B, preferably so that the bearing housings can only be engaged and disengaged at one of the two ends of the rails.

A friction lock 3 is also connected to bearing housing 12A through slot 32 in side shield 15. Friction lock 3 can be used to limit the linear motion speed (including limiting the speed of travel of or stopping the linear motion for a given amount of force imposed by an operator of the apparatus) of bearing housing 12A as well as top panel 14 and those components attached thereto.

As included previously, the end of the arm 2 attached to the linear slide apparatus at position 7. Position 7 may include a hollow sleeve 33 attached to top panel 14 and a collar 34 which is positioned inside hollow sleeve 33. Collar 34 may include a linear cavity 35 through the length thereof with an opening 36 through which electrical and other connective wires and cables are fed that lead through arm 2 to x-ray source 16. An embodiment can include collar 34 being fixed within hollow sleeve 33 or such that collar 34 can have rotational motion relative to hollow sleeve 33. This structure may also provide an attachment to post 37 to which arm 2 may be attached via, for example, a pin 38 passing though post 37 and arm 2 such that arm 2 can pivot around pin 38.

Linear slide apparatus 1 is secured to post 6 (an attachment structure) to which it is mounted to the main base 18. The mounting apparatus may include stationary shaft 39 and sleeve structural tube 40 which are connected using eye bolt 41 that is connected to structural tube 40 and passes through a central passage 57 in stationary shaft 39. Another embodiment can include a similar structure where structural tube 40 is stationary and shaft 39 is moveable. In between stationary shaft 39 and sleeve structural tube 40 may be a plurality of washers and bearings including, for example, bearing washers 42, thrust bearings 43, sleeve bearing 44 and steel washer 45. Steel screw 46 can also pass through a hole in structural tube 40 for holding stationary shaft 39 within the tube. Sleeve bearing 44 runs over stationary shaft 39 to allow rotational movement.

A friction lock 11 is also connected to through a hole 58 in bottom structure plate 13A to engage and limit rotational motion of the linear slide apparatus 1 relative to the main base 18. Friction lock 11 can be used to limit the rotational motion speed (including limiting the speed of travel of or stopping the rotational motion for a given amount of force imposed by an operator of the apparatus) of linear slide apparatus 1 and those components attached thereto.

FIG. 8 illustrates an exemplary embodiment of a moveable x-ray source unit 17 that includes a base 18, a linear slide 1 and a vertically moving arm 2. The base 18 may include various electrical, power, computer and other systems used to control and optionally power to the x-ray source unit 16 and the x-ray detector 56 (an x-ray operation and control system). Various cables, electrical and other conduits may pass from the base 18 up through column 47, linear slide 1 and arm 2 to x-ray source 16. X-ray source unit 17 also includes computer monitor or display 48 and an x-ray detector 56 (for example, a digital x-ray detector and a flat panel x-ray detector including a flat panel x-ray digital detector). As used herein, the term "display" or "monitor" means any type of device adapted to display information, including without limitation CRTs, LCDs, TFTs, plasma displays, LEDs, and fluorescent devices. Computer monitor 48 can be physically attached to column 47 and electrically connected to base 18 and in communication with the various electrical, power, computer and other systems housed therein, can be moveable from the base 18 and physically attached to and electrically connected (e.g., hard wired) to base 18 and in communication with the various electrical, power, computer and other systems housed therein or can be independent from base 18 as well as independently powered (e.g. a battery or separate power source) and wirelessly connected to and in communication with (e.g., WIFI, Bluetooth, etc.) the various electrical, computer and other systems housed therein. X-ray detector 56 can be moveable from the base 18 and physically attached to and electrically connected (e.g., hard wired) to base 18 and in communication with the various electrical, power, computer and other systems housed therein or can be independent from base 18 as well as independently powered (e.g. a battery or separate power source) and wirelessly connected 59 to and in communication with (e.g., WIFI, Bluetooth, etc.) the various electrical, computer and other systems housed therein. Moveable x-ray source 17 also includes a plurality of wheels 49 or other suitable attachment to permit movement thereof, for example, four wheels, one located at the corners of base 18, if the bottom 50 of base 18 is generally square in shape positioned parallel to the floor.

FIGS. 7 and 8 illustrate the linear movement along path 20, the rotational movement around axis 21 and vertical movement of arm 2 and the x-ray source attached to it 51 of for example, about 75°. As a result of the linear slide apparatus 1, the arm 2 and attached x-ray source 16 can be raised from the position shown in FIG. 8 so has to reduce the vertical footprint to be within the area of the base 18 should the sides of base 18 be extended upwards. As a result, the moveable x-ray source unit 17 can be manoeuvred in the tight quarters of, for example, a neonatal unit where there is minimal floor space due to the presence of incubators and other hospital equipment taking up floor space.

The embodiment of FIG. 8 may also include a mounting arm 52 which is connected to arm 2 and may allow pivot up and down of x-ray source 16 relative to arm 2 at position 53. Mounting arm 52 may be connected to x-ray source 16 at position 54 and may allow axial rotation of x-ray source around position 54 relative to mounting arm 52.

Thus, while there have been shown and described and pointed out fundamental novel features of the invention as applied to the exemplary embodiments thereof, it will be understood that various omissions and substitutions and changes in the form and details of devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

What is claimed is:

1. A linear slide apparatus for an x-ray source where the x-ray source is mounted to a first end of an arm, comprising:
a top panel to which a second end of the arm is pivotally mounted to the top panel such that the arm and x-ray source attached thereto can be moved up and down within an arc;
two linear rails;
two bearing housings each slideably engaged with one of the linear rails to produce a linear movement along the path of the linear rails, the two bearing housings connected to the top panel; and a linear slide base to which the linear rails are mounted, the linear slide base also attached to a structural base unit via an attachment structure capable of permitting rotational movement of the linear slide base around the structural base unit.

2. The linear slide apparatus of claim 1, further including a first friction lock engaged with at least one of the bearing housing to control the sliding motion of the one bearing housing to which it is engaged.

3. The linear slide apparatus of claim 1, wherein the linear slide base comprises:
   a bottom structural plate attached to the structural base unit; and
   two side structural plates each attached to the bottom structural plate on opposing sides thereof and attached to the two linear rails.

4. The linear slide apparatus of claim 1, wherein the linear movement and the rotational movement is manually caused and controlled by an operator.

5. The linear slide apparatus of claim 1, wherein the x-ray source is placed in plurality of spatial positions relative to the structural base unit using the linear movement and the rotational movement of the linear slide apparatus.

6. The linear slide apparatus of claim 1, wherein the linear slide apparatus is part of a portable x-ray unit.

7. The linear slide apparatus of claim 1, further including a second friction lock engaged with the attachment structure capable of permitting rotational movement of the linear slide base around the structural base unit to control the rotational movement of the linear slide apparatus.

8. A portable x-ray unit, comprising:
   an arm;
   an x-ray source mounted to a first end of an arm;
   a linear slide apparatus, comprising:
      a top panel to which a second end of the arm is pivotally mounted to the top panel such that the arm and x-ray source attached thereto can be moved up and down within an arc;
      two linear rails;
      two bearing housings each slideably engaged with one of the linear rails to produce a linear movement along the path of the linear rails, the two bearing housings connected to the top panel; and
      a linear slide base to which the linear rails are mounted;
   a moveable structural base unit to which the linear slide base is attached via an attachment structure capable of permitting rotational movement of the linear slide base around the moveable structural base unit;
   a monitor and
   an x-ray detector.

9. The portable x-ray unit of claim 8, wherein the x-ray detector is a flat panel x-ray detector.

10. The portable x-ray unit of claim 8, wherein the linear slide base comprises:
    a bottom structural plate attached to the structural base unit; and
    two side structural plates each attached to the bottom structural plate on opposing sides thereof and attached to the two linear rails.

11. The portable x-ray unit of claim 8, wherein the linear movement and the rotational movement is manually caused and controlled by an operator.

12. The portable x-ray unit of claim 8, wherein the x-ray source is placed in plurality of spatial positions relative to the moveable structural base unit using the linear movement and the rotational movement of the linear slide apparatus.

13. The portable x-ray unit of claim 8, further including a first friction lock engaged with at least one of the bearing housing to control the sliding motion of the one bearing housing to which it is engaged.

14. The portable x-ray unit of claim 8, further including a second friction lock engaged with the attachment structure capable of permitting rotational movement of the linear slide base around the structural base unit to control the rotational movement of the linear slide apparatus.

15. The portable x-ray unit of claim 8, wherein the moveable structural base includes a plurality of wheels to facilitate movement of the portable x-ray unit.

16. The portable x-ray unit of claim 8, wherein the x-ray source is pivotally mounted to the first end of the arm to permit the up and down movement of the x-ray source relative to the arm.

17. The portable x-ray unit of claim 8, wherein the moveable structural base unit includes an x-ray operation and control system used to control the x-ray source unit and the x-ray detector.

18. A portable x-ray unit, comprising:
    an arm;
    an x-ray source mounted to a first end of an arm;
    a linear slide apparatus, comprising:
       a top panel to which a second end of the arm is pivotally mounted to the top panel such that the arm and x-ray source attached thereto can be moved up and down within an arc;
       two linear rails;
       two bearing housings each slideably engaged with one of the linear rails to produce a linear movement along the path of the linear rails, the two bearing housings connected to the top panel; and
       a linear slide base to which the linear rails are mounted;
    a monitor;
    an x-ray detector; and
    a moveable structural base unit to which the linear slide base is attached via an attachment structure capable of permitting rotational movement of the linear slide base around the moveable structural base unit, the moveable structural base unit including an x-ray operation and control system used to control the x-ray source unit and the x-ray detector, where the x-ray detector is hard wired or wirelessly in communication with the x-ray operation and control system.

19. The portable x-ray unit of claim 18, wherein the x-ray detector is a flat panel x-ray digital detector.

* * * * *